United States Patent
Feth et al.

(10) Patent No.: US 10,434,605 B2
(45) Date of Patent: Oct. 8, 2019

(54) METHOD FOR PRODUCING A BODY IMPLANT, ASSEMBLY CONSISTING OF A GUIDE WIRE AND A BODY IMPLANT, AND A MEDICAL INSTRUMENT

(71) Applicant: Admedes Schuessler GmbH, Pforzheim (DE)

(72) Inventors: Nils-Agne Feth, Waldbronn (DE); Alexander Lange, Karlsruhe (DE); Ralf Steiner, Pforzheim (DE)

(73) Assignee: ADMEDES SCHUESSLER GMBH, Pforzheim (DE)

( * ) Notice: Subject to any disclaimer, the term of this patent is extended or adjusted under 35 U.S.C. 154(b) by 421 days.

(21) Appl. No.: 14/404,336

(22) PCT Filed: Jan. 22, 2013

(86) PCT No.: PCT/EP2013/000185
§ 371 (c)(1),
(2) Date: Dec. 10, 2014

(87) PCT Pub. No.: WO2013/178297
PCT Pub. Date: Dec. 5, 2013

(65) Prior Publication Data
US 2015/0165558 A1    Jun. 18, 2015

(30) Foreign Application Priority Data
May 30, 2012   (DE) .......... 10 2012 010 687

(51) Int. Cl.
*A61F 2/01*    (2006.01)
*A61B 17/221*  (2006.01)
(Continued)

(52) U.S. Cl.
CPC .......... *B23K 26/364* (2015.10); *A61B 17/221* (2013.01); *A61F 2/01* (2013.01);
(Continued)

(58) Field of Classification Search
CPC .......... A61B 17/221; A61B 2017/2212; A61B 2017/2215; A61B 2017/2217; A61F 2/01;
(Continued)

(56) References Cited

U.S. PATENT DOCUMENTS 5,376,100 A * 12/1994 Lefebvre ........ A61B 17/320725
604/22
5,495,668 A *  3/1996 Furusawa ............... B21F 45/00
257/E23.067
(Continued)

FOREIGN PATENT DOCUMENTS

DE  197 22 429 A1  12/1998
DE  197 45 294 A1   4/1999

OTHER PUBLICATIONS

International Search Report and Written Opinion for PCT/EP2013/000185, dated Apr. 4, 2013, 10 pages.
(Continued)

*Primary Examiner* — Dianne Dornbusch
(74) *Attorney, Agent, or Firm* — Harrity & Harrity, LLP

(57) ABSTRACT

The invention relates to a method for producing a body implant comprising the steps of: providing a wire; producing predetermined cuts of the cross section of the wire by means of an ultrashort pulse laser in order to produce a predetermined shape of the body implant. This method can be used to produce, for example, a body implant, an assembly consisting of a guide wire and a body implant, or a medical instrument having a guide wire.

17 Claims, 8 Drawing Sheets

(51) Int. Cl.
| | |
|---|---|
| *B23K 26/364* | (2014.01) |
| *A61F 2/91* | (2013.01) |
| *B23K 26/0622* | (2014.01) |
| *A61F 2/89* | (2013.01) |
| *B23K 101/32* | (2006.01) |
| *A61B 17/00* | (2006.01) |

(52) U.S. Cl.
CPC ................ *A61F 2/89* (2013.01); *A61F 2/91* (2013.01); *B23K 26/0624* (2015.10); *A61B 2017/00526* (2013.01); *A61B 2017/00867* (2013.01); *A61B 2017/2212* (2013.01); *A61F 2002/018* (2013.01); *A61F 2210/0014* (2013.01); *A61F 2230/005* (2013.01); *A61F 2230/0097* (2013.01); *A61F 2240/001* (2013.01); *B23K 2101/32* (2018.08)

(58) Field of Classification Search
CPC . A61F 2/91; A61F 2002/011; A61F 2002/018
See application file for complete search history.

(56) References Cited

U.S. PATENT DOCUMENTS

| | | | | |
|---|---|---|---|---|
| 5,573,520 | A * | 11/1996 | Schwartz | A61M 25/0013 604/264 |
| 5,707,387 | A * | 1/1998 | Wijay | A61F 2/91 606/194 |
| 5,916,235 | A * | 6/1999 | Guglielmi | A61B 17/12022 606/194 |
| 5,980,514 | A * | 11/1999 | Kupiecki | A61B 17/12022 604/104 |
| 6,022,369 | A * | 2/2000 | Jacobsen | A61B 17/12022 606/1 |
| 6,160,240 | A | 12/2000 | Momma et al. | |
| 6,190,402 | B1 * | 2/2001 | Horton | A61B 17/12118 606/108 |
| 6,258,117 | B1 * | 7/2001 | Camrud | A61F 2/82 623/1.16 |
| 6,299,612 | B1 * | 10/2001 | Ouchi | A61B 18/14 606/113 |
| 6,398,791 | B1 * | 6/2002 | Que | A61B 17/221 604/264 |
| 6,402,771 | B1 * | 6/2002 | Palmer | A61B 17/221 606/114 |
| 6,551,342 | B1 * | 4/2003 | Shen | A61F 2/01 606/200 |
| 6,579,246 | B2 * | 6/2003 | Jacobsen | A61M 25/09 600/585 |
| 6,893,450 | B2 * | 5/2005 | Foster | A61B 17/221 606/200 |
| 7,060,083 | B2 * | 6/2006 | Gerberding | A61B 17/12022 606/191 |
| 7,377,925 | B2 * | 5/2008 | Poll | A61B 17/22012 606/128 |
| 7,524,322 | B2 * | 4/2009 | Monstdt | A61B 17/12022 606/194 |
| 7,632,242 | B2 * | 12/2009 | Griffin | A61B 17/22032 604/102.01 |
| 7,771,410 | B2 * | 8/2010 | Venturelli | A61M 25/0054 604/523 |
| 7,828,832 | B2 * | 11/2010 | Belluche | A61F 2/95 623/1.11 |
| 7,850,708 | B2 * | 12/2010 | Pal | A61F 2/013 606/200 |
| 7,857,008 | B2 * | 12/2010 | Chen | A61M 25/09 138/109 |
| 7,914,466 | B2 * | 3/2011 | Davis | A61M 25/0013 600/585 |
| 7,914,467 | B2 * | 3/2011 | Layman | A61M 25/0013 600/585 |
| 8,016,870 | B2 * | 9/2011 | Chew | A61F 2/88 623/1.11 |
| 8,251,963 | B2 * | 8/2012 | Chin | A61M 25/0084 604/272 |
| 8,292,827 | B2 * | 10/2012 | Musbach | A61M 25/0054 600/585 |
| 8,323,241 | B2 * | 12/2012 | Salahieh | A61M 25/0136 604/95.04 |
| 8,409,114 | B2 * | 4/2013 | Parins | A61M 25/00 600/585 |
| 8,523,879 | B1 * | 9/2013 | Lind | A61B 17/221 606/113 |
| 8,529,596 | B2 * | 9/2013 | Grandfield | A61B 17/320725 606/127 |
| 8,708,953 | B2 * | 4/2014 | Salahieh | A61B 1/00135 604/95.01 |
| 8,795,254 | B2 * | 8/2014 | Layman | A61B 1/00071 600/585 |
| 8,821,477 | B2 * | 9/2014 | Northrop | A61M 25/0013 600/139 |
| 8,876,772 | B2 * | 11/2014 | Weber | A61L 29/041 604/164.01 |
| 8,961,550 | B2 * | 2/2015 | Lenker | A61B 17/3417 606/185 |
| 9,011,480 | B2 * | 4/2015 | Divino | A61B 17/12031 606/200 |
| 9,067,332 | B2 * | 6/2015 | Lippert | A61M 25/0009 |
| 9,067,333 | B2 * | 6/2015 | Lippert | A61M 25/0009 |
| 9,072,874 | B2 * | 7/2015 | Northrop | A61M 25/001 |
| 9,144,665 | B2 * | 9/2015 | Salstrom | A61M 25/0138 |
| 9,149,609 | B2 * | 10/2015 | Ansel | A61B 17/22031 |
| 9,717,612 | B2 * | 8/2017 | Dorn | A61F 2/95 |
| 9,795,307 | B2 * | 10/2017 | Radman | A61B 5/02154 |
| 9,795,765 | B2 * | 10/2017 | Romoscanu | A61M 25/0013 |
| 2001/0041899 | A1 * | 11/2001 | Foster | A61B 17/221 606/127 |
| 2002/0010481 | A1 * | 1/2002 | Jayaraman | A61B 17/0057 606/151 |
| 2002/0065553 | A1 | 5/2002 | Weber | |
| 2004/0138677 | A1 * | 7/2004 | Little | A61B 17/221 606/127 |
| 2005/0182390 | A1 | 8/2005 | Shanley | |
| 2007/0010762 | A1 * | 1/2007 | Ressemann | A61M 25/09 600/585 |
| 2007/0043413 | A1 * | 2/2007 | Eversull | A61N 1/057 607/122 |
| 2007/0067019 | A1 * | 3/2007 | Miller | A61F 2/856 623/1.16 |
| 2007/0112373 | A1 * | 5/2007 | Carr, Jr. | A61F 2/01 606/200 |
| 2007/0142901 | A1 * | 6/2007 | Steinke | A61F 2/94 623/1.16 |
| 2007/0225729 | A1 * | 9/2007 | Cheng | A61B 17/221 606/127 |
| 2008/0039930 | A1 * | 2/2008 | Jones | A61B 17/12022 623/1.15 |
| 2008/0208211 | A1 * | 8/2008 | Uihlein | A61B 17/221 606/127 |
| 2008/0312597 | A1 * | 12/2008 | Uihlein | A61M 25/09 604/164.13 |
| 2009/0088832 | A1 * | 4/2009 | Chew | A61F 2/88 623/1.12 |
| 2009/0248133 | A1 * | 10/2009 | Bloom | A61F 2/2418 623/1.15 |
| 2010/0102046 | A1 | 4/2010 | Huang et al. | |
| 2010/0168758 | A1 * | 7/2010 | Uihlein | A61B 17/00234 606/127 |
| 2010/0318115 | A1 * | 12/2010 | Chanduszko | A61F 2/01 606/200 |
| 2011/0009950 | A1 * | 1/2011 | Grandfield | A61F 2/91 623/1.16 |
| 2011/0070358 | A1 | 3/2011 | Mauch et al. | |
| 2011/0160838 | A1 * | 6/2011 | Blanzy | A61L 27/042 623/1.13 |
| 2011/0245907 | A1 | 10/2011 | Pacetti | |
| 2011/0288630 | A1 * | 11/2011 | Blanzy | A61C 7/20 623/1.15 |

(56) References Cited

U.S. PATENT DOCUMENTS

| | | | |
|---|---|---|---|
| 2011/0319988 A1* | 12/2011 | Schankereli | A61F 2/2418 |
| | | | 623/2.11 |
| 2012/0046687 A1* | 2/2012 | Trommeter | A61B 17/12022 |
| | | | 606/200 |
| 2013/0289701 A1* | 10/2013 | Coghlan | A61F 2/07 |
| | | | 623/1.13 |
| 2018/0008439 A9 | 1/2018 | Tieu et al. | |

OTHER PUBLICATIONS

Official Communication for corresponding EP Application No. 13 703 522.6-1651, dated Apr. 22, 2014, 5 pages.
International Preliminary Report on Patentability for PCT/EP2013/000185, dated Dec. 11, 2014, 6 pages.

* cited by examiner

METHOD FOR PRODUCING A BODY IMPLANT, ASSEMBLY CONSISTING OF A GUIDE WIRE AND A BODY IMPLANT, AND A MEDICAL INSTRUMENT

The present invention relates to a method for producing a body implant, an assembly consisting of a guide wire and a body implant, and a medical instrument.

Conventionally, body implants and medical instruments, such as stents, baskets, filters or catching devices are made of hollow round material, like e.g. a tube. Alternatively or additionally, such devices may be produced by braiding wires. This measure, however, involves high production expenditure, and devices produced in this way have a limited crimp capability, i.e. a capability of reducing their diameter for insertion into the human body. Thus, there is need for a method and for devices produced by this method, having a higher crimp capability and a simpler production method.

Thus, the object of the invention is to provide a simplified method and corresponding devices which simplify the production of stents, baskets, filters and the like, and which allow for higher crimp capability.

This object is accomplished by the features of the independent claims. Advantageous embodiments of the invention are defined in the dependent claims.

According to one aspect, the invention relates to a method for producing a body implant, comprising the steps of:
providing a wire,
producing cuts, or notches, or structures, respectively, on the wire's cross section using an ultrashort pulse laser, in order to produce a predetermined shape of the body implant.

Preferably, the cuts are produced substantially in radial direction, and a cut portion of the wire, or a wire segment, is expanded in order to produce a body implant, such as a closed basket or a filter, stent or the like.

A part, preferably the major part of the wire's cross section can be removed by the cuts, for example, in order to produce a joint.

Still preferentially, the method can further include the step of braiding wire segments and/or a step of shaping wire segments.

Preferably, a wire is used which is made of a material having shape-memory properties, such as Nitinol.

The ultrashort pulse laser technology allows for micro treatment of materials, such as wires without having to expel the removed material, such as re-solidified mass in the case of conventional laser fusion cutting. Hence, a process of cold removal, a so-called ablation process, takes place. In contrast to conventional laser fusion cutting where only continuous cuts can be made, there is the possibility of structuring a wire, on the one hand, thus altering the mechanical and/or electrical or electronic properties. On the other hand, this process allows for slitting very fine wires symmetrically as well as asymmetrically by cuts. Thus, by producing radial cuts in the wire, wire segments can be separated from the wire, and subsequently can be shaped and/or expanded in order to produce a basket, a stent, or a filter, for example. Moreover, the wire segments can be braided in order to systematically manipulate mechanical and electrical or electronic properties.

Moreover, the cuts or notches or structures, respectively, can be produced such that an integrally formed joint is produced from the wire by means of removing a major part of the cross section. Thus, numerous configurations are possible by means of generating corresponding cuts on a wire using the ultrashort pulse laser technology.

According to a further aspect, the invention relates to an assembly consisting of a guide wire and a body implant produced by means of such a method, with the guide wire and the body implant being integrally, or monolithically, formed and having a predetermined breaking point. Herein, the guide wire can have at least an integrally formed joint in order to increase the flexibility or bending property of the guide wire.

Preferably, the assembly has at least one of a stent, a basket or a filter.

According to a further aspect, a medical instrument having a guide wire is provided that is produced using this method. Therein, the guide wire can have at least an integrally formed joint.

The advantage of this manufacturing technology is that an assembly consisting of a guide wire and a body implant, or a medical instrument, respectively, can be made of one piece, such that connecting a guide wire with a body implant by means of micro welding, for example, is no longer necessary. Thus, a fault susceptibility of a corresponding assembly consisting of a guide wire and a medical instrument is considerably reduced.

This integrally formed assembly can have a predetermined breaking point such that the body implant, or the medical instrument, is separated from the guide wire after positioning in the human body in order to remove the guide wire. Further, the production process is highly simplified. Moreover, the guide wire can have an integrally formed joint in order to provide higher flexibility.

This technology has the advantage of having lower raw material costs, is mechanically stronger and has maximal crimp capability, since the expanded wire segments can be deformed or crimped so as to assume the original position of the uncut wire, in order to reduce the diameter for insertion into the human body to a minimal diameter. Moreover, the device can be produced with a minimal number of production steps.

The invention will now be explained in more detail based on exemplary embodiments with reference to the accompanying drawings.

Figure 1:
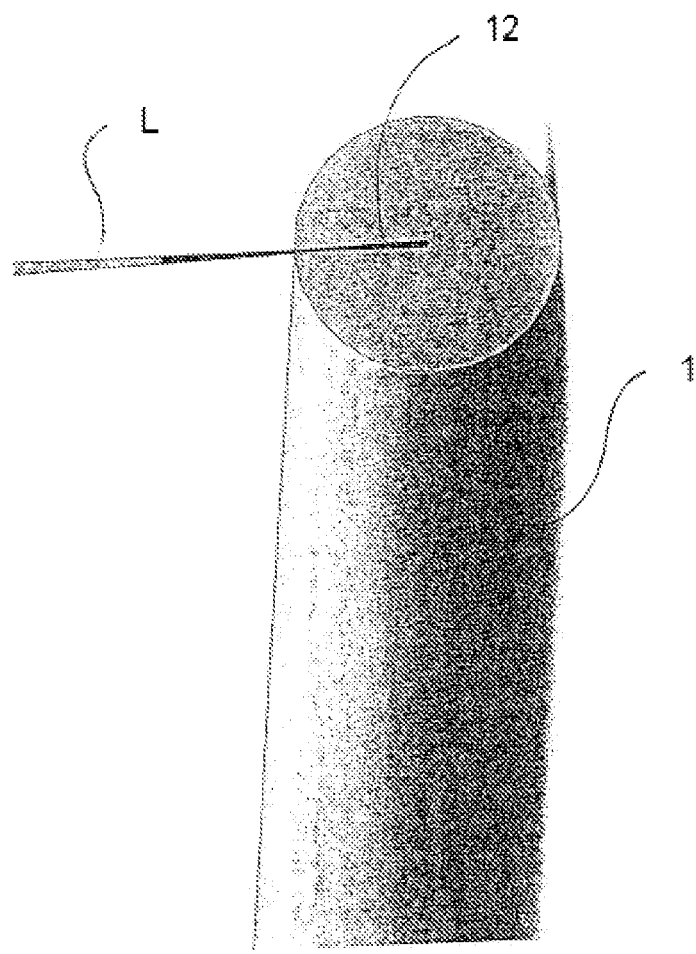
FIG. 1 shows a circular wire being cut by a laser beam in radial direction approximately up to its center.

As shown in FIG. 1, a circular wire 1 is cut in up to approximately the center thereof by means of a laser beam L using the ultrashort pulse laser technology, in order to generate a cut 12. Although circular wires are advantageously used for this technology, the invention is not restricted thereto. Wires having elliptical cross sections, triangular, square, pentagon wires, or the like can also be used.

Advantageously, an ultrashort pulse laser having a wavelength of about 200 to about 2000 nm is used therein. The pulse width should be about 10 fs to about 10 ps.

Figure 2:
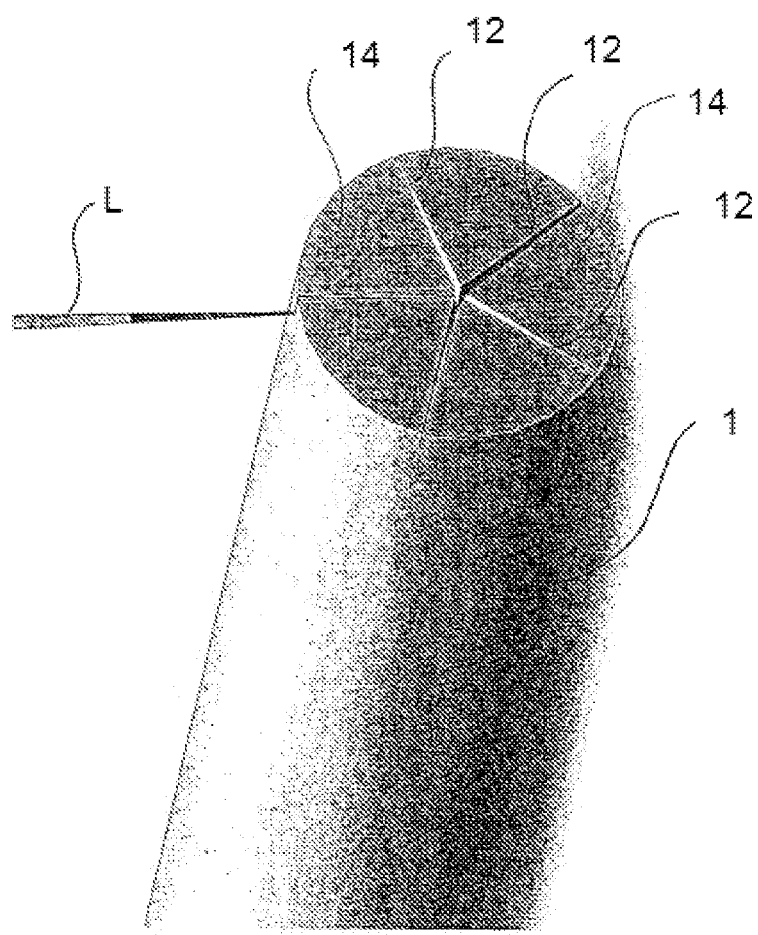
FIG. 2 shows the production of five cuts in total in a radial direction up to the wire's center.
Figure 3:
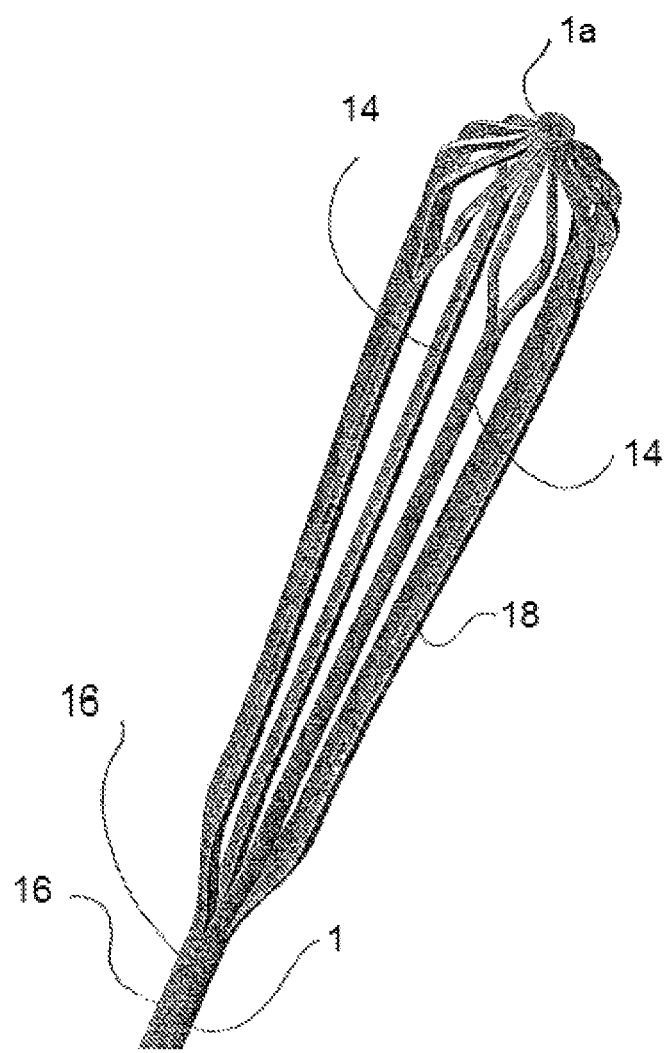
FIG. 3 shows a design of a basket or filter produced by the cuts wherein the cut wire segments are subsequently expended.

Further, for example, five radial cuts extending to the center of the wire can be generated, in order to produce wire segments or cut sectors 14, as shown in FIG. 2. These cut sectors or wire segments 14 subsequently can be expanded by deformation so as to produce, for example, a basket or filter design, as shown for example in FIG. 3. Therein, the cuts do not extend up to an axial end 1a, 1b of the wire 1, such that the individual wire segments 14 remain connected in longitudinal directions at their ends.

In this manner, a basket or filter design, respectively, is produced having wire segments 14 which are integrally connected at their ends 1a, 1b.

This means that the wire 1 is divided, like a pie, into individual segments (wire segments 14), wherein axial ends 1a, 1b of the wire are not separated. The separated wire segments 14 are expanded such that a body is generated having spaced wire segments 14 in the axial center and axial ends 1a, 1b which are integrally connected to the wire segments 14.

It should be appreciated that the invention can also be realized with three, four, six or seven cuts 12, etc. Therein, the cuts 12 do not have to be set at regular angular distances, but "pieces of pie", or wire segments 14, of different sizes can be generated.

Figure 8A:
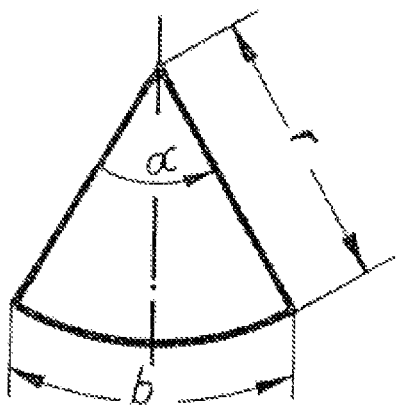
FIG. 8a shows a wire segment formed as a circle sector.
Figure 8B:
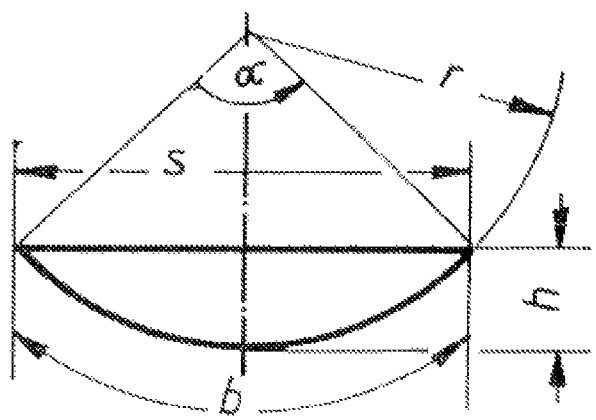
FIG. 8b shows a wire segment formed as a circle segment.

Moreover, the wire segments 14 do not have to be generated as a circle sector having the length of the radius r of the wire 1 as sides of the circle sector, i.e. by means of cuts 12 ending at the center of the wire cross-section, as shown in FIG. 8a, but any forms can be separated from the wire cross-section, such as a circle segment, as shown for example in FIG. 8b.

A circle segment, as shown in FIG. 8b, is separated from the wire cross-section by producing a cut 12 offset from the center of the wire cross-section along the chord length s. Therein, a height h of the cut 12 is smaller than the radius r of the wire.

By means of separating wire segments 14 with different cross sections from the wire cross-section in this manner, and expanding them subsequently, a stent can be generated, for example, having varying supporting powers along the circumference thereof.

These wire segments 14 can be deformed or treated according to the desired mechanical and/or electrical properties by further shaping by means of forming or by further laser treatment. Moreover, the wire segments 14 can be braided, e.g. by tatting the wire segments with the weave types 1/2, 1/1, or 2/2.

Figure 4:
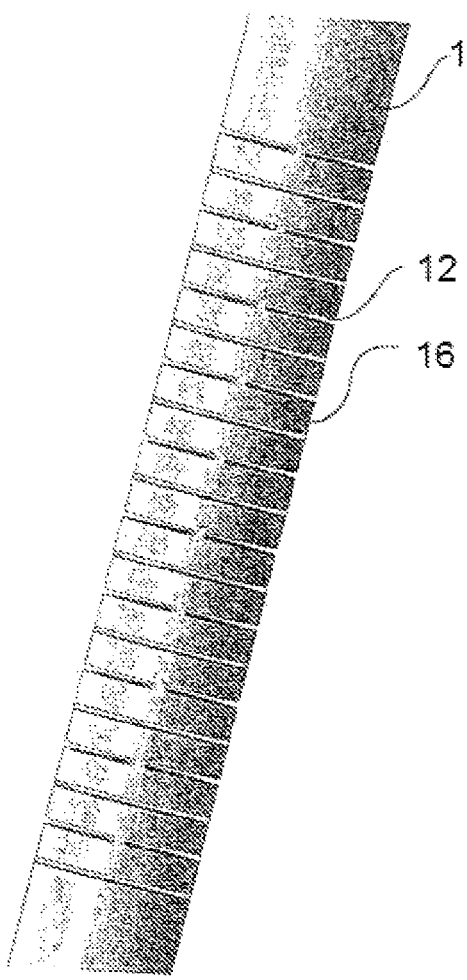
FIG. 4 shows a guide wire exhibiting high bending property or flexibility due to the generation of corresponding cuts.
Figure 5:
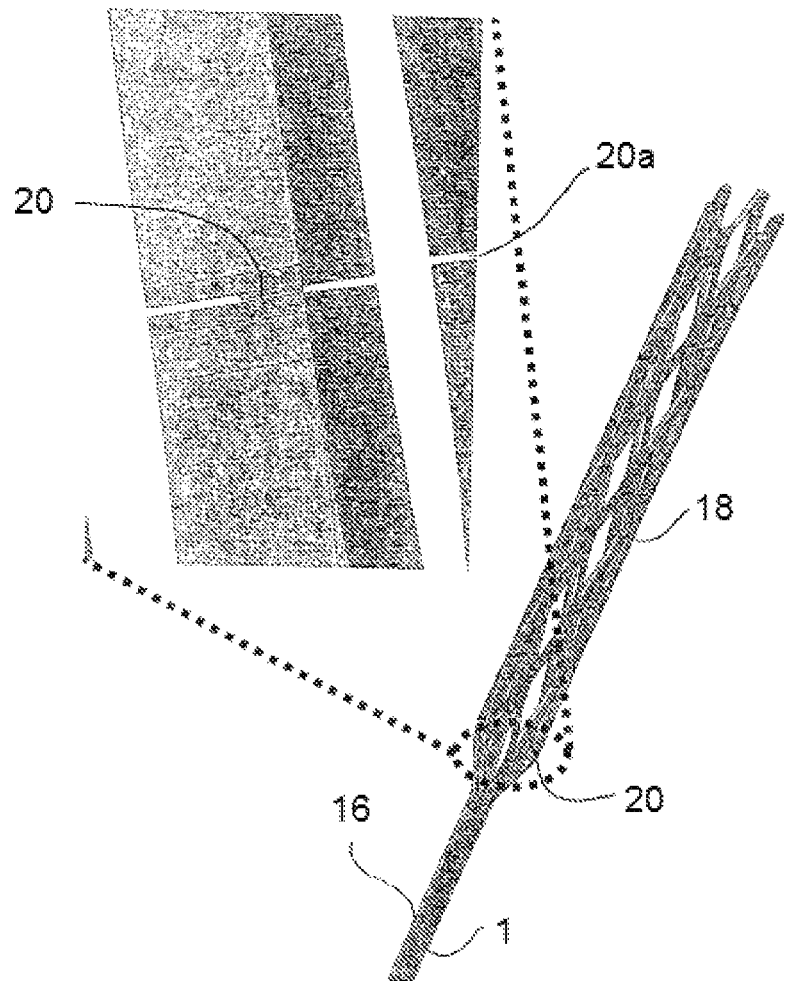
FIG. 5 shows a stent integrally formed with the guide wire and having a predetermined breaking point.

The basket or filter design, or stent 18, respectively, produced this way can subsequently be separated from the wire 1. It can, however, also remain connected to a longer piece of wire 1 such that the uncut end of the wire 1 is used as a guide wire 16, as shown for example in FIGS. 4 and 5.

A predetermined breaking point 20 can be provided between the guide wire 16 and the body implant 18 generated, such that the assembly consisting of the guide wire 16 and the body implant 18, which is integrally formed in this manner, can be separated at the predetermined breaking point 20 after insertion and positioning of the body implant 18, in order to remove the guide wire 16 after positioning of the body implant 18. Therein, the guide wire 16 can have corresponding cuts 12 or sectional weakenings or structures, respectively, in order to provide for high flexibility or bending property. The predetermined breaking point 20 has a corresponding sectional weakening 20a, in order to facilitate breaking or separating at the predetermined breaking point 20.

Figure 6:
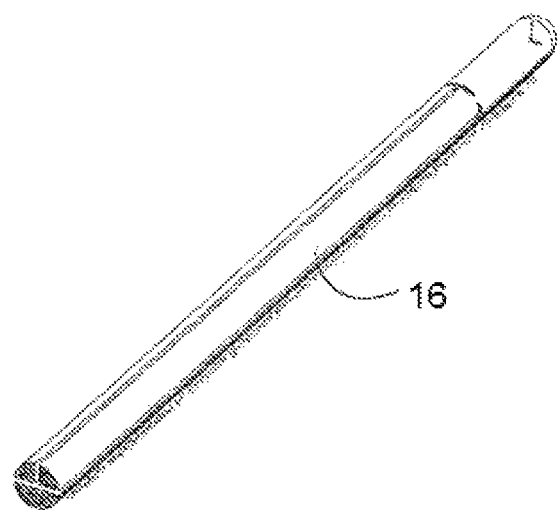
FIG. 6 shows a controllable guide wire.
Figure 7:
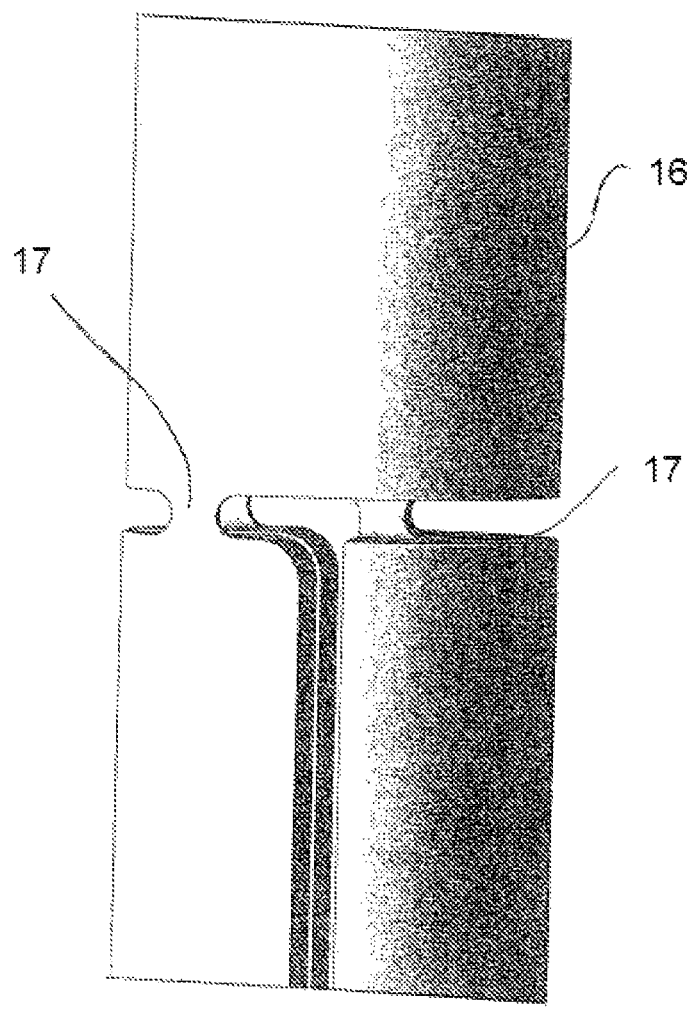
FIG. 7 shows a detailed view of the guide wire of FIG. 6 with a corresponding joint for bending the guide wire.

As further shown in FIGS. 6 and 7, a corresponding joint 17 can be produced by a cut wherein almost the whole cross section of the wire or guide wire 16, respectively, is removed, around which joint one end of the guide wire 16 can be bent with respect to another segment.

Thus a variety of design possibilities is provided by correspondingly cutting a wire 1 using the ultrashort pulse laser technology, and by expanding and, if applicable, further treating the cut wire segments 14. Thus, a body implant 18, e.g. a stent, a basket, or a filter can be produced as one piece in a simple manner. Moreover, this body implant 18 can be crimped to the original wire diameter in order to achieve maximal reduction of diameter.

Preferably, a wire 1 is used which is made of a material having shape-memory properties, such as Nitinol. However, other metals or nonmetals can also be employed.

The invention is not limited to the production of radial cuts 12, but cuts can be made also in other directions. Moreover, the cuts 12 do not have to reach the center of the wire 1, but depending on the application can be produced with less or more depth. Structures or notches on the cross section of the wire 1 can be generated thereby.

LIST OF REFERENCE SIGNS 1 wire
12 cut
14 wire segment
16 guide wire
17 joint
18 body implant (stent)
20 predetermined breaking point
20a sectional weakening
L laser

The invention claimed is:
1. An assembly consisting of:
a guide wire; and
a body implant,
wherein the guide wire and the body implant are integrally formed and have a predetermined breaking point,
wherein wire segments are separated from the guide wire, via radial cuts in the guide wire, and are expanded to shape the body implant,
wherein the wire segments are braided from tatting the wire segments,
where the guide wire comprises a first portion, a second portion, and an integrally formed joint for flexibility,
where the integrally formed joint is between the first portion and the second portion, and
wherein the integrally formed joint is narrower than the first portion and the second portion.

2. The assembly according to claim 1, wherein the body implant has at least one of a stent, a basket, or a filter.

3. The assembly according to claim 1, wherein the radial cuts are produced by means of an ultrashort pulse laser.

4. The assembly according to claim 1, wherein a removal of a portion of a cross section of the guide wire produces the integrally formed joint.

5. The assembly according to claim 1, wherein the guide wire is made of a material having shape-memory properties.

6. The assembly according to claim 1, wherein the wire segments remain connected to the guide wire at least while the wire segments are expanded to shape the body implant.

7. The assembly according to claim 1, wherein the radial cuts extend to a center of the guide wire.

8. The assembly according to claim 1, wherein a height of a cut, of the radial cuts, is smaller than a radius of the guide wire.

9. The assembly according to claim 1, wherein a diameter of the body implant is equal to or less than an original diameter of the guide wire.

10. A medical instrument comprising:
   a guide wire with radial cuts that are produced by means of an ultrashort pulse laser,
      wherein wire segments are separated, from a wire that is used for the guide wire,
   as a result of the radial cuts that are produced by means of the ultrashort pulse laser,
      wherein the wire segments are braided by tatting the wire segments,
      wherein the wire segments are expanded to shape a body implant,
      where the guide wire comprises a first portion, a second portion, and an integrally formed joint for flexibility,
      where the integrally formed joint is between the first portion and the second portion, and
      wherein the integrally formed joint is narrower than the first portion and the second portion.

11. The medical instrument according to claim 10, wherein the guide wire and the body implant are integrally formed and have a predetermined breaking point.

12. The medical instrument according to claim 10, where the body implant comprises one of a stent, a basket, or a filter.

13. The medical instrument according to claim 10, wherein a removal of a portion of a cross section of the guide wire produces the integrally formed joint.

14. The medical instrument according to claim 10, wherein the guide wire is made of a material having shape-memory properties.

15. The medical instrument according to claim 10, wherein the body implant is connected to the guide wire before being separated from the guide wire.

16. The medical instrument according to claim 10, wherein the body implant is crimped to an original diameter of the guide wire.

17. The medical instrument according to claim 10, wherein the wire segments are tatted with a weave type of 1/2, 1/1, or 2/2.

* * * * *